(12) United States Patent
Sévigny

(10) Patent No.: US 9,250,208 B2
(45) Date of Patent: Feb. 2, 2016

(54) ELECTROPHORESIS BUFFER FOR EXTENDING THE USEFUL ELECTROPHORESIS LIFE OF AN ELECTROPHORESIS GEL

(75) Inventor: M. Pierre Sévigny, Montréal (CA)

(73) Assignee: DGEL ELECTROSYSTEM INC., Montreal (CA)

( * ) Notice: Subject to any disclaimer, the term of this patent is extended or adjusted under 35 U.S.C. 154(b) by 320 days.

(21) Appl. No.: 13/547,633

(22) Filed: Jul. 12, 2012

(65) Prior Publication Data

US 2013/0015067 A1    Jan. 17, 2013

Related U.S. Application Data

(60) Provisional application No. 61/507,883, filed on Jul. 14, 2011.

(51) Int. Cl.
*G01N 27/447* (2006.01)
(52) U.S. Cl.
CPC ................. *G01N 27/44747* (2013.01)
(58) Field of Classification Search
CPC ................................ G01N 27/44747
USPC .............. 204/468, 606, 616, 456, 466
See application file for complete search history.

(56) References Cited

U.S. PATENT DOCUMENTS

| | | | |
|---|---|---|---|
| 4,246,084 A * | 1/1981 | Gurske | 204/468 |
| 5,275,708 A | 1/1994 | Akins, Jr. et al. | |
| 5,464,517 A | 11/1995 | Hjertén et al. | |
| 6,096,182 A | 8/2000 | Updyke et al. | |
| 6,726,821 B1 | 4/2004 | Suzuki | |
| 2002/0162744 A1 | 11/2002 | Nouadje | |
| 2002/0195341 A1 | 12/2002 | Robert | |
| 2005/0121325 A1* | 6/2005 | Updyke et al. | 204/469 |
| 2005/0269267 A1 | 12/2005 | Patton et al. | |
| 2009/0034334 A1 | 2/2009 | Furuyama et al. | |
| 2011/0000788 A1 | 1/2011 | Deschamps | |
| 2011/0073478 A1* | 3/2011 | Updyke et al. | 204/616 |

FOREIGN PATENT DOCUMENTS

| | | |
|---|---|---|
| EP | 494686 A | 7/1992 |
| WO | WO2004011513 A1 | 2/2004 |
| WO | 2011028535 A2 | 3/2011 |
| WO | WO2011134072 A1 | 11/2011 |

OTHER PUBLICATIONS

International Search Authority, International Search Report (ISR), Oct. 16, 2012, 3 pages.
European Search Report of EP12812090.4; Munich; Oct. 27, 2014; Peter Komenda.

(Continued)

*Primary Examiner* — J. Christopher Ball
(74) *Attorney, Agent, or Firm* — Benoit & Cote Inc.

(57) ABSTRACT

There is provided an electrolyte solution for extending useful electrophoresis life of an electrophoresis gel containing Tris (hydroxymethyl)aminomethane (TRIS), at least one zwitterion, and water. The electrolyte solution may be used in buffer systems for gel electrophoresis, such as SDS-PAGE.

23 Claims, 4 Drawing Sheets

(56) References Cited

OTHER PUBLICATIONS

Applichem: "Take the Pink Link!", https://www.applichem.com/fileadmin/Broschueren/BioBuffer.pdf, Jan. 1, 2008, XP055148764, Retrieved from the internet: URL:https://www.applichem.com/fileadmin/Broschueren/BioBuffer.pdf, P:[retrieved on Oct. 24, 2014].

Anonymous: "SERVA Tris-MOPS/SDS Electrophoresis Buffer (20x)", Internet Citation, May 1, 2007, pp. 1-3, XP008159698, Retrieved from the Internet: URL:https://web.archive.org/web/20110712170842//https://www.serva.de/www_root/documents/42561_e.pdf, [retrieved on Jan. 28, 2013].

Chinese Office Action from corresponding application No. 201280034735.5; May 6, 2015.

* cited by examiner

Aged Novex® Tris-Glycine Gels with Electrolyte solution containing EPPS. All gels ran in 1X fresh buffer at 125V, as recommended by the manufacturer.

| Gel % | Expiry date | Cat # | Lot # | Run time EPPS | Run quality EPPS | Photo EPPS | Run time TGS | Run quality TGS | Photo TGS |
|---|---|---|---|---|---|---|---|---|---|
| 4-12% | 31 Dec 08 | EC6035 | 8091022 | 55' | ++ | | 100' | - | Gel distorted and broken inside the cassette |
| 4-12% | 05 Nov 10 | EC6035 | 10071671 | 55' | +++ | | 100' | (+) | |
| 4-20% | 03 May 11 | EC6025 | 11022270 | 55' | +++ | | 100' | +++ | |
| 10% | 28 May 11 | EC6075 | 11020550 | 55' | +++ | | 100' | ++(+) | |

Fig. 1

ELECTROPHORESIS BUFFER FOR EXTENDING THE USEFUL ELECTROPHORESIS LIFE OF AN ELECTROPHORESIS GEL

CROSS-REFERENCE TO RELATED APPLICATIONS

This application claims priority under 35 USC §119(e) of U.S. provisional patent application No. 61/507,883, filed on Jul. 14, 2011, the specification of which is hereby incorporated by reference.

BACKGROUND (a) Field

The subject matter disclosed generally relates to gel electrophoresis. More specifically, the subject matter disclosed relates to an electrolyte solution for extending the useful electrophoresis life of an electrophoresis gel during gel electrophoresis containing at least one zwitterion, and water.

(b) Related Prior Art

Gel electrophoresis is a common procedure for the separation of biological molecules, such as deoxyribonucleic acid (DNA), ribonucleic acid (RNA), polypeptides and proteins. In gel electrophoresis, the molecules are separated into bands according to the rate at which an imposed electric field causes them to migrate through a filtering gel.

The basic apparatus used in this technique consists of a gel enclosed in a glass tube, sandwiched as a slab between glass or plastic plates, or poured in a plastic tray. The gel has an open molecular network structure, defining pores which are saturated with an electrically conductive buffered solution. These pores through the gel are large enough to admit passage of the migrating macromolecules.

The gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel.

The most common buffer system employed for the separation of proteins is the Laemmli buffer system consists of 0.375 M tris(hydroxy methyl)amino-methane (Tris), titrated to pH 8.8 with HCl, in the separating gel. The stacking gel consists of 0.125 M Tris, titrated to pH 6.8. The anode and cathode running buffers contain 0.024 M Tris, 0.192 M glycine, 0.1% SDS. Many different gel separation materials have been disclosed, with different compositions, pH characteristics, voltage requirements, etc. The goal of most of the recent innovations in the field has been to provide an electrophoresis gel which can be used to perform a faster, more accurate, more stable, or therefore more versatile electrophoresis.

A number of different gel buffer systems have been proposed for use at or around neutral pH that do not involve the use of the Tris-HCl Glycine buffer system of Laemmli.

For example, U.S. Pat. No. 6,096,182 to Updyke et al. discloses an electrophoresis gel at a neutral pH. The advantage of producing such a gel is that the gel system is stable, with reduced reactivity and increased shelf life.

U.S. Pat. No. 5,464,517 to Hjerten et al. discloses an electrophoresis buffer which has a high buffering capacity and low electrical conductivity. The advantage of this type of buffer, particularly in capillary electrophoresis, is that it allows the separation to be performed at a higher voltage and consequently more quickly.

A majority of innovations have focused on improving electrophoresis by proposing new recipes for the gel buffer.

Currently, a major obstacle in the production and sale of pre-cast electrophoresis gels is their rather short shelf life of about 3 months. For example, for pre-cast polyacrylamide gels, it is believed that their degradation is a consequence of the hydrolysis of amide groups to form partially anionic carboxylic acid derivatives under basic conditions. Therefore, the high pH (e.g. pH 8.0 to 9.5) is believed to lower the stability of the gels upon storage. The hydrolysis is believed to lead to loss of resolution of the separated molecules, reduced migration distance of the separated molecule, and the reduced intensity of protein staining.

Therefore, there is a need for reagents that will extend the useful electrophoresis life of gels that have gone pass their normal expiry date (shelf-life).

SUMMARY

In a first embodiment there is disclosed an electrolyte solution for extending a useful electrophoresis life of an electrophoresis gel comprising:

at least one zwitterion chosen from 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino]ethanesulphonic acid) (TES), N-Tris(hydroxymethyl)methyl-3-aminopropanesulfonic acid (TAPS) and 3-N-Morpholino propanesulfonic acid (POPSO); and water.

The zwitterion may be 4-(2-hydroxyethyl)piperazine-1-propanesulfonic acid (EPPS or HEPPS).

The zwitterion may be chosen from N-Glycylglycine (Gly-Gly) and 3-(cyclohexylamino)-2-hydroxy-1-propanesulfonic acid (CAPSO).

The pH is of the electrolyte solution may be from about 8.0 to about 11.

The electrolyte solution may be further comprising Tris (hydroxymethyl)aminomethane (TRIS).

The electrolyte solution may be further comprising sodium dodecyl sulphate (SDS).

The electrolyte solution may further be comprising a chelating agent having the name: ethylenediaminetetraacetate (EDTA), ethylene glycol tetraacetic acid (EGTA), trisodium nitrilotriacetate, hydroxyethyl ethylenediamine trisodium acetate (trisodium HEDTA), diethylene triamino pentasodium acetate or uramil disodium acetate.

The concentration of Tris(hydroxymethyl)aminomethane (TRIS) may be from about 10 mM to about 500 mM.

The concentration of Tris(hydroxymethyl)aminomethane (TRIS) may be from about 50 mM to about 150 mM.

The concentration of Tris(hydroxymethyl)aminomethane (TRIS) may be from about 50 mM to about 300 mM.

The concentration of Tris(hydroxymethyl)aminomethane (TRIS) may be 150 mM.

The concentration of the zwitterion may be from about 1 mM to about 500 mM.

The concentration of the zwitterion may be from about 10 mM to about 500 mM.

The concentration of the zwitterion may be from about 25 mM to about 75 mM.

The concentration of the zwitterion may be from about 50 mM to about 100 mM.

The concentration of the zwitterion may be 50 mM.

The concentration of the zwitterion may be 100 mM.

The concentration of sodium dodecyl sulphate (SDS) may be 0.5% (wt/vol) or less.

The concentration of sodium dodecyl sulphate (SDS) may be 0.1% (wt/vol) or less.

The concentration of sodium dodecyl sulphate (SDS) may be 0.1% (wt/vol).

The concentration of ethylenediaminetetraacetate (EDTA) may be 0.5% (wt/vol) or less.

The concentration of ethylenediaminetetraacetate (EDTA) may be 0.05% (wt/vol) or less.

The concentration of ethylenediaminetetraacetate (EDTA) may be 0.03% (wt/vol).

According to another embodiment, there is disclosed a method of extending a useful electrophoresis life of an electrophoresis gel during an electrophoretic separation of at least one sample comprising the step of:

applying a voltage to an electrolyte solution according to the present invention in contact with an electrophoresis gel containing the at least one sample therein.

According to another embodiment, there is disclosed a method of extending a useful electrophoresis life of an electrophoresis gel during an electrophoretic separation of at least one sample comprising the step of:

adding at least one zwitterion chosen from 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis (hydroxymethyl)ethylamino]ethanesulphonic acid) (TES), N-Tris(hydroxymethyl)methyl-3-aminopropanesulfonic acid (TAPS) and 3-N-Morpholino propanesulfonic acid (POPSO) to an electrophoresis buffer.

The zwitterion may be 4-(2-hydroxyethyl)piperazine-1-propanesulfonic acid (EPPS or HEPPS).

The zwitterion may be chosen from N-Glycylglycine (Gly-Gly) and 3-(cyclohexylamino)-2-hydroxy-1-propanesulfonic acid (CAPSO).

The method of the present invention may be further comprising the step of applying a voltage to the electrophoresis buffer in contact with an electrophoresis gel containing the at least one sample therein.

The following terms are defined below.

The term "improved resolution" is intended to mean a better resolution which allows separation of sharper or narrower bands of molecules, distanced or spaced apart from each other as opposed to other means of separation which have broader or thicker bands. This facilitates physical separation or molecular weight identification of the different molecules that make up these bands over the entire range of molecular weight.

The term "useful electrophoresis life" is intended to mean the normal operating life of an electrophoresis gel in terms of utility to the owner. This covers the period of time during which there is no unacceptable loss of electrophoretic quality of the electrophoresis gel (e.g. loss of resolution, decrease in migration speed, migration artefacts, over-heating polyacrylamide gel, gel cracking or distortion, etc.); and during which the electrophoresis gel remains usable for its intended purpose.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

FIG. 1 illustrates polyacrylamide gels electrophoresed in electrolyte solutions according embodiments of the present invention and compared to a gel electrophoresed on Trisglycine-SDS (baseline) solution. All the gels electrophoreses were pass their expiry date.

DETAILED DESCRIPTION OF THE PREFERRED EMBODIMENTS

Figure 2:
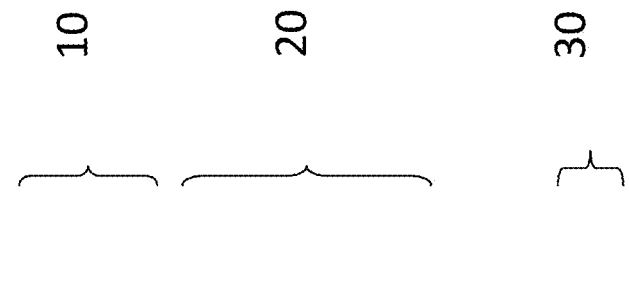
FIG. 2 illustrates polyacrylamide gels electrophoresed in electrolyte solutions according embodiments of the present invention and compared to a gel electrophoresed on Trisglycine-SDS (baseline) solution. All the gels electrophoreses were pass their expiry date.
Figure 2:
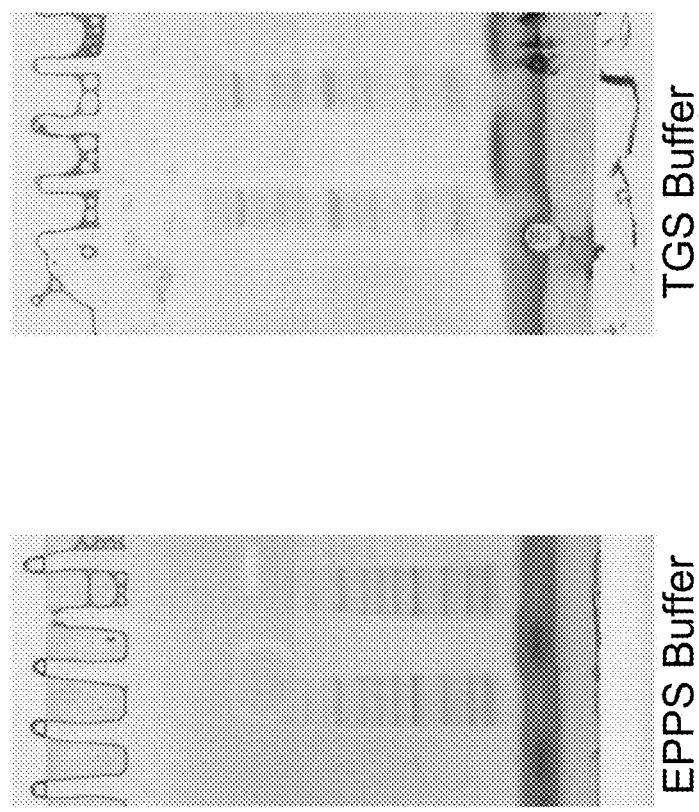

The present inventors have now surprisingly found that selecting specific zwitterions to prepare an electrolyte solution for use in gel electrophoresis can result in the unexpected extension of the useful life of electrophoresis gel for their use in electrophoresis (or as also used herein, electrophoretic separation). This new and unexpected property is in addition to any other property that the specific zwitterions identified may have, for example provide increases in electrophoresis speed, improvements in gel resolution, or both. This improvement may be observed, for example, when the electrolyte solutions are used as running buffer (also referred to as "reservoir" buffer) for the electrophoresis apparatus in which electrophoresis gels that have gone pass their expected expiry date are employed for electrophoresis.

In embodiments there are disclosed electrolyte solutions for performing gel electrophoresis. The electrolyte contains specific components.

Zwitterions

A zwitterion is a chemical compound that carries a total net charge of 0 and is thus electrically neutral, but carries formal charges on different atoms. Zwitterions are polar and are usually very water-soluble, but poorly soluble in most organic solvents. Zwitterions will exist mostly as zwitterions in a certain range of pH. The pH at which the average charge is zero is known as the molecule's isoelectric point.

The zwitterions of interest in the present invention belong to the category commonly referred to as biological buffers, which are buffers that are commonly used as buffering agents in biological laboratories. Examples of biological buffers that can be cited are those known as bis-TRIS(2-bis[2-hydroxyethyl]amino-2-hydroxymethyl-1,3-propanediol), ADA (N-[2-acetamido]-2-iminodiacetic acid), ACES (2-[2-acetamino[-2-aminoethanesulphonic acid), PIPES (1,4-piperazinediethanesulphonic acid), MOPSO (3-[N-morpholino]-2-hydroxypropanesulphonic acid), bis-TRIS PROPANE (1,3-bis[tris(hydroxymethyl)methylaminopropane]), BES (N,N-bis[2-hydroxyethyl]-2-aminoethanesulphonic acid), MOPS (3-[N-morpholino]propancsulphonic acid), TES (2-[2-hydroxy-1,1-bis(hydroxymethyl)ethylamino]ethanesulphonic acid), HEPES (N-[2-hydroxyethyl] piperazine-N'-(2-ethanesulphonic)acid), DIPSO (3-N,N-bis[2-hydroxyethyl]amino-2-hydroxypropanesulphonic acid), MOBS (4-N-morpholinobutanesulphouic acid), TAPSO (3[N-tris-hydroxymethyl-methylamino]-2-hydroxypropanesulphonic acid), TRIS(2-amino-2-[hydroxymethyl]-1,3-propanediol), H EPPSO (N-[2-hydroxyethyl]piperazine-N'-[2-hydroxypropanesulphonic]acid), POPSO (piperazie-N,N'-bis[2-hydroxypropanesulphonic]acid), TEA (triethanolamine), EPPS (or HEPPS) (N-[2-hydroxyethyl]-piperazine-N'-[3-propanesulphonic]acid), TRICINE (N-tris[hydroxymethyl]methylglycine), GLY-GLY (diglycine), BICINE (N,N-bis[2-hydroxyethyl]glycine), HEPBS (N-[2-hydroxyethyl]piperazine-N'-[4-butanesulphonic]acid), TAPS (N-tris[hydroxymethyl]methyl-3-aminopropanesulphonic acid), AMPD (2-amino-2-methyl-1,3-propanediol), TABS (N-tris[hydroxymethyl]methyl-4-aminobutanesulphonic acid), AM PSO (3-[(1,1-dimethyl-2-hydroxyethyl)amino]-2-hydroxypropanesulphonic acid), CHES (2-(N-cyclohexylamino)ethanesulphonic acid), CAPSO (3-[cyclohexylamino]-2-hydroxy-1-propanesulphonic acid), AMP (2-amino-2-methyl-1-propanol), CAPS (3-cyclohexylamino-1-propanesulphonic acid), and CABS (4-[cyclohexylamino]-1-butanesulphonic acid).

Although the biological buffering property of these zwitterions has been recognized, the capacity of a select group of these zwitterions to positively impact the performance of gel electrophoresis, and the useful electrophoresis life of gels for gel electrophoresis was not.

Preferably the zwitterions include 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino]ethanesulphonic acid) (TES), N-Tris(hydroxymethyl)methyl-3-aminopropanesulfonic acid (TAPS) and 3-N-Morpholino propanesulfonic acid (POPSO). These zwitterions significantly improve the useful electrophoresis life of electrophoresis gels that have gone pass their expiry date when the electrolyte solutions are used as running buffer (also referred to as "reservoir" buffer) for the electrophoresis apparatus in which electrophoresis is being performed. The zwitterion may also be added to existing running buffers. When using these zwitterions in the electrolyte solution according to the present invention, it may be desirable to adjust the pH of the electrolyte solution (e.g using NaOH or HCl) to an optimal pH value for performing the electrophoresis.

According to another embodiment, these zwitterions may also improve the speed at which electrophoresis may be performed (as compared to the classical Tris-Glycine-SDS at pH 8.3 of Laemmli), improve resolution (as compared to the classical Tris-Glycine-SDS at pH 8.3 of Laemmli) by improving the definition (or sharpness), by providing thinner or narrow bands) of the molecules separated, by improving the separation between the molecules (i.e. the distance between the individual bands, or by both improving the definition (or sharpness) and separation of the molecules. Also, when used for the preparation of gels, increase in the shelf life of gels prepared using these electrolyte solutions. The zwitterions may be used alone or in combination.

The ranges of concentration over which these zwitterions may be used for the preparation of electrolyte solutions according to the present invention, for extending the useful electrophoresis life as discussed herein are from about 1 mM to about 500 mM, or from about 10 mM to about 500 mM, or about 25 mM to about 500 mM, or about 50 mM to about 500 mM, or about 75 mM to about 500 mM, or about 100 mM to about 500 mM, or about 150 mM to about 500 mM, or about 200 mM to about 500 mM, or about 250 mM to about 500 mM, or about 300 mM to about 500 mM, or about 350 mM to about 500 mM, or about 400 mM to about 500 mM, or about 450 mM to about 500 mM, 1 mM to about 450 mM, or from about 10 mM to about 450 mM, or about 25 mM to about 450 mM, or about 50 mM to about 450 mM, or about 75 mM to about 450 mM, or about 100 mM to about 450 mM, or about 150 mM to about 450 mM, or about 200 mM to about 450 mM, or about 250 mM to about 450 mM, or about 300 mM to about 450 mM, or about 350 mM to about 450 mM, or about 400 mM to about 450 mM, 1 mM to about 400 mM, or from about 10 mM to about 400 mM, or about 25 mM to about 400 mM, or about 50 mM to about 400 mM, or about 75 mM to about 400 mM, or about 100 mM to about 400 mM, or about 150 mM to about 400 mM, or about 200 mM to about 400 mM, or about 260 mM to about 400 mM, or about 300 mM to about 400 mM, or about 350 mM to about 400 mM, 1 mM to about 375 mM, or from about 10 mM to about 375 mM, or about 25 mM to about 375 mM, or about 50 mM to about 375 mM, or about 75 mM to about 375 mM, or about 100 mM to about 375 mM, or about 150 mM to about 375 mM, or about 200 mM to about 375 mM, or about 260 mM to about 375 mM, or about 300 mM to about 375 mM, or about 350 mM to about 375 mM, or 1 mM to about 350 mM, or from about 10 mM to about 350 mM, or about 25 mM to about 350 mM, or about 50 mM to about 350 mM, or about 75 mM to about 350 mM, or about 100 mM to about 350 mM, or about 150 mM to about 350 mM, or about 200 mM to about 350 mM, or about 260 mM to about 350 mM, or about 300 mM to about 350 mM, 1 mM to about 300 mM, or from about 10 mM to about 300 mM, or about 25 mM to about 300 mM, or about 50 mM to about 300 mM, or about 75 mM to about 300 mM, or about 100 mM to about 300 mM, or about 150 mM to about 300 mM, or about 200 mM to about 300 mM, or about 260 mM to about 300 mM, 1 mM to about 260 mM, or from about 10 mM to about 260 mM, or about 25 mM to about 260 mM, or about 50 mM to about 260 mM, or about 75 mM to about 260 mM, or about 100 mM to about 260 mM, or about 150 mM to about 260 mM, or about 200 mM to about 260 mM, 1 mM to about 200 mM, or from about 10 mM to about 200 mM, or about 25 mM to about 200 mM, or about 50 mM to about 200 mM, or about 75 mM to about 200 mM, or about 100 mM to about 200 mM, or about 150 mM to about 200 mM, 1 mM to about 150 mM, or from about 10 mM to about 150 mM, or about 25 mM to about 150 mM, or about 50 mM to about 150 mM, or about 75 mM to about 150 mM, or about 100 mM to about 150 mM, 1 mM to about 100 mM, or from about 10 mM to about 100 mM, or about 25 mM to about 100 mM, or about 50 mM to about 100 mM, or about 75 mM to about 100 mM, 1 mM to about 75 mM, or from about 10 mM to about 75 mM, or about 25 mM to about 75 mM, or about 50 mM to about 75 mM, 1 mM to about 50 mM, or from about 10 mM to about 50 mM, or about 25 mM to about 50 mM, 1 mM to about 25 mM, or from about 10 mM to about 25 mM, or from about 1 mM to about 10 mM, or from about 25 mM to about 50 mM, or from about 25 mM to about 100 mM, or from about 10 mM to about 100 mM, or from about 1 mM to about 100 mM, or from about 1 mM to about 75 mM, or from about 10 mM to about 75 mM, or from about 1 mM to about 10 mM, or from about 1 mM to about 50 mM or from about 10 mM to about 50 mM, or from about 25 mM to about 375 mM, and preferably, at 100 mM.

Optimal results with 4-(2-hydroxyethyl)piperazine-1-propanesulfonic acid (EPPS or HEPPS) are obtained at pH of about pH 8.0 to 10.5.

Tris(Hydroxymethyl)Aminomethane Base (TRIS)

Tris is an abbreviation of the organic compound known as tris(hydroxymethyl)aminomethane, with the formula $(HOCH_2)_3CNH_2$. Tris is extensively used in biochemistry and molecular biology. In biochemistry, Tris is widely used as a component of buffer solutions, such as in TAE and TBE buffer, especially for solutions of nucleic acids and is the basic element of the Laemmli buffer widely used in protein electrophoresis in Tris-Glycine buffers.

Tris also allows the pH of the electrolyte solution of the present invention to be set towards more basic pH values. According to one embodiment, an electrolyte solution according to the present invention containing EPPS at 47.5 mM may have a pH of about 5.9. The addition of Tris (about 150 mM) increases the pH at about 8.7. Tris also has a positive impact on the migration speed in the preferred concentration ranges.

Tris may be absent from the electrolyte solution of the present invention. However, the ranges of concentration over which Tris base may be used for the preparation of electrolyte solutions according to the present invention are from about 0 mM to about 500 mM. The Tris concentration has a direct impact on the pH of the solution. An increasing amount of Tris increases the pH. This allow fine adjustments in adapting the electrolyte solution of the present invention to different gel chemistry and keeping a proper pH ratio compatible with gel and buffer. The concentrations of Tris may be from about 0 mM to about 500 mM, or from about 10 mM to about 500 mM, or about 25 mM to about 500 mM, or about 50 mM to about 500 mM, or about 75 mM to about 500 mM, or about 100 mM to about 500 mM, or about 150 mM to about 500 mM, or about 200 mM to about 500 mM, or about 250 mM to about 500 mM, or about 300 mM to about 500 mM, or about 350 mM to about 500 mM, or about 400 mM to about 500 mM, or about 450 mM to about 500 mM, or from about 0 mM to about 450 mM, or from about 10 mM to about 450 mM, or about 25 mM to about 450 mM, or about 50 mM to about 450 mM, or about 75 mM to about 450 mM, or about 100 mM to about 450 mM, or about 150 mM to about 450 mM, or about 200 mM to about 450 mM, or about 260 mM to about 450 mM, or about 300 mM to about 450 mM, or about 350 mM to about 450 mM, or about 400 mM to about 450 mM, or from about 0 mM to about 400 mM, or from about 10 mM to about 400 mM, or about 25 mM to about 400 mM, or about 50 mM to about 400 mM, or about 75 mM to about 400 mM, or about 100 mM to about 400 mM, or about 150 mM to about 400 mM, or about 200 mM to about 400 mM, or about 260 mM to about 400 mM, or about 300 mM to about 400 mM, or about 350 mM to about 400 mM, or from about 0 mM to about 375 mM, or from about 10 mM to about 375 mM, or about 25 mM to about 375 mM, or about 50 mM to about 375 mM, or about 75 mM to about 375 mM, or about 100 mM to about 375 mM, or about 150 mM to about 375 mM, or about 200 mM to about 375 mM, or about 260 mM to about 375 mM, or about 300 mM to about 375 mM, or about 350 mM to about 375 mM, or from about 0 mM to about 350 mM, or from about 10 mM to about 350 mM, or about 25 mM to about 350 mM, or about 50 mM to about 350 mM, or about 75 mM to about 350 mM, or about 100 mM to about 350 mM, or about 150 mM to about 350 mM, or about 200 mM to about 350 mM, or about 260 mM to about 350 mM, or about 300 mM to about 350 mM, or from about 0 mM to about 300 mM, or from about 10 mM to about 300 mM, or about 25 mM to about 300 mM, or about 50 mM to about 300 mM, or about 75 mM to about 300 mM, or about 100 mM to about 300 mM, or about 150 mM to about 300 mM, or about 200 mM to about 300 mM, or about 260 mM to about 300 mM, or from about 0 mM to about 260 mM, or from about 10 mM to about 250 mM, or about 25 mM to about 260 mM, or about 50 mM to about 260 mM, or about 75 mM to about 260 mM, or about 100 mM to about 260 mM, or about 150 mM to about 260 mM, or about 200 mM to about 260 mM, or from about 0 mM to about 200 mM, or from about 10 mM to about 200 mM, or about 25 mM to about 200 mM, or about 50 mM to about 200 mM, or about 75 mM to about 200 mM, or about 100 mM to about 200 mM, or about 150 mM to about 200 mM, or from about 0 mM to about 150 mM, or from about 10 mM to about 150 mM, or about 25 mM to about 150 mM, or about 50 mM to about 150 mM, or about 75 mM to about 150 mM, or about 100 mM to about 150 mM, or from about 0 mM to about 100 mM, or from about 10 mM to about 100 mM, or about 25 mM to about 100 mM, or about 50 mM to about 100 mM, or about 75 mM to about 100 mM, or from about 0 mM to about 75 mM, or from about 10 mM to about 75 mM, or about 25 mM to about 75 mM, or about 50 mM to about 75 mM, or from about 0 mM to about 50 mM, or from about 10 mM to about 50 mM, or about 25 mM to about 50 mM, or from about 0 mM to about 25 mM, or from about 10 mM to about 25 mM, or about 25 mM to about 50 mM, or from about 25 mM to about 100 mM, or from about 10 mM to about 100 mM, or from about 10 mM to about 75 mM, or from about 10 mM to about 50 mM, or from about 25 mM to about 375 mM. Preferably the concentration of Tris is from about 50 mM to about 375 mM, and preferably 150 mM.

Sodium Dodecyl Sulfate or Other Anionic Surfactants

Sodium dodecyl sulfate (SDS) $(C_{12}H_{25}SO_4Na)$ is an anionic surfactant is commonly used in preparing proteins for electrophoresis in the SDS-PAGE technique. The molecule has a tail of 12 carbon atoms, attached to a sulfate group, giving the molecule the amphiphilic properties required of a detergent.

SDS may be optionally added to the electrolyte solution of the present invention. The superior results obtained with the electrolyte solutions according to the present invention are obtained independently of the presence of SDS. The ranges of concentration over which SDS may be used for the preparation of electrolyte solutions according to the present invention, for all the applications discussed herein are from about 0.5% or less or from about 0.4% or less or from about 0.3% or less or from about 0.2% or less, or from about 0.1% or less, or from about 0.1% to about 0.5%, or from about 0.2% to about 0.5%, or from about 0.3% to about 0.5%, or from about 0.4% to about 0.5%, or from about 0.1% to about 0.4%, or from about 0.2% to about 0.4%, or from about 0.3% to about 0.4%, or from about 0.1% to about 0.3%, or from about 0.2% to about 0.3%, or from about 0.1% to about 0.2%. Preferably, from about 0.1% or less, and most preferably, at 0.1%.

Other anionic surfactants may be included in the electrolyte solution of the present invention, such as, in a non-limiting manner facultative, one anionic surfactant to provide to the buffer denaturing properties for protein analysis: SDS, sodium dodecyl sulphate, lithium dodecyl sulphate (LDS), sodium lauryl sulfate (SLS), sodium laurilsulfate or sodium, NaDS. The ranges of concentration over which they may be used for the preparation of electrolyte solutions according to the present invention, for all the applications discussed herein are from 1.0% or less. Preferably, from about 0.1% or less, and most preferably, at about 0.1%.

Chelating Agents

Ethylenediaminetetraacetate (EDTA) has a role as a chelating agent, i.e. its ability to "sequester" metal ions such as $Ca^{2+}$ and $Fe^{3+}$. After being bound by EDTA, metal ions remain in solution but exhibit diminished reactivity. Other chelating agents may include ethylene glycol tetraacetic acid (EGTA), trisodium nitrilotriacetate, hydroxyethyl ethylenediamine trisodium acetate (trisodium HEDTA), diethylene triamino pentasodium acetate or uramil disodium acetate.

EDTA may be optionally added to the electrolyte solution of the present invention. The ranges of concentration over which EDTA may be used for the preparation of electrolyte solutions according to the present invention, for all the applications discussed herein are from about 0.5% or less, or from about 0.4% or less, or from about 0.3% or less, or from about 0.2% or less, or from about 0.1% or less, or from about 0.05% or less, or from about 0.03% to about 0.5%, or from about 0.05% to about 0.5% or from about 0.1% to about 0.5%, or from about 0.2% to about 0.5%, or from about 0.3% to about 0.5%, or from about 0.4% to about 0.5%, or from about 0.03% to about 0.4%, or from about 0.05% to about 0.4% or from about 0.1% to about 0.4%, or from about 0.2% to about 0.4%, or from about 0.3% to about 0.4%, or from about 0.03% to about 0.3%, or from about 0.05% to about 0.3% or from about 0.1% to about 0.3%, or from about 0.2% to about 0.3%, or from about 0.03% to about 0.5%, or from about 0.05% to about 0.2% or from about 0.1% to about 0.2%, or from about 0.03% to about 0.1%, or from about 0.05% to about 0.1%, or from about 0.03% to about 0.05%. Preferably, from about 0.05% or less, and most preferably, at 0.03%.

Use of the Electrolyte Solutions

In use the electrolyte solutions of the present invention is compatible with a very wide range of other buffer systems. The electrolyte solution of the present invention may be used to run electrophoresis of gels of any type, prepared with the same or with different buffer systems than that of the present invention, even including gels using different chemistries, such as MOPS as a buffer (such as those described in US Patent publication No. 20060118418), under the appropriate conditions.

According to the present invention, electrophoresis includes the separation of samples of DNA or protein or any other type of molecule that may be separated accordingly, as well as their transfer onto membranes or other suitable solid support such has nitrocellulose, nylon, PVDF or other types of membranes that are commonly used for applications such as Western transfer and blotting.

The electrolyte solution according to the present invention may be used in electrophoresis chambers and/or systems of commercial make. For examples, Invitrogen™ Surelock™, BioRad™ Mini-Protean®, Protean® 2, Protean® III, Protean® Tetra. Other equivalent systems also functions as well.

The electrolyte solution of the present invention may be used as the buffer system in most of gels used in molecular biology and biochemistry, as described in classical references such as: Uriel 1966, Bull. Soc. Chem. Biol. 48:969; Peacock & Dingman 1967, Biochem 6(6), 1818-1827; Peacock & Dingman 1968, Biochem 7(2), 668-674; Gaal, Electrophoresis in the separation of biological macromolecules, p 422, Wiley, 1980. The electrolyte solutions of the present invention may be included in acrylamide gels (polyacrylamide gels), under native (without SDS) or denaturing conditions (with SDS) that are typically prepared with acrylamide concentrations from about 4% to about 25%. The electrolyte solutions of the present invention may be included in agarose gels that are typically prepared with agarose concentrations from about 0.5% to about 3%.

EPPS (or HEPPS), TAPS, TES, BES or Glygly can be added to the Laemmli buffer Tris-Glycine-SDS at a working concentration of 25 mM to 150 mM and preferably at 50 mM and extend the useful electrophoresis life of electrophoresis gels.

Alternative Embodiments

Example 1

Gel Electrophoresis of Novex® Precast Gels

An electrolyte solution according to the present invention is prepared to be used with polyacrylamide gels made using classic recipes such as the Laemmli buffer system (Tris-Glycine-SDS). The exemplary electrolyte solution:

Zwitterion: EPPS: 6 g (47.5 mM), Tris (Base): 9 g (148.6 mM), SDS: 0.5 g (0.1%). The powders are dissolved in distilled water up to a volume of 500 mL.

500 ml of running buffer were prepared with a zwitterion according to the present invention as well as with a classic running buffer according to the Laemmli buffer system (Tris-Glycine-SDS). Age matched precast gel from NOVEX® (made with Tris pH 8.3 as buffering solution and glycine, according to the Leammli buffer system) that are pass their expiry date (as shown in FIG. 1) are run against each buffer. Protein molecular weight markers are separated on the electrophoresis gels. The electrophoresis is performed at 125V as recommended by the manufacturer of the gel. The duration of the electrophoretic run is recorded, and the quality gel migration is scored. After the electrophoretic run, the migration speed for the migration front to reach the bottom of the gel, and the resolution of a prestained molecular weight marker containing 10 bands weighing between 15 KDa to 175 KDa is measured. The resolution of each of these bands of the gel run in the electrolyte solution according to the present invention is compared to the standard run in the Laemmli running buffer (Tris-Glycine-SDS, TGS). The results show that gels pass their expiry date for over 3 years ran more than acceptably in the solution of the present invention, while the older gels ran in the classic TGS solution disintegrated during migration in the case of the oldest gel, or displayed clear migration artifacts (see the gel images in FIG. 1, last column in the second and fourth lines).

Example 2

Gel Electrophoresis of Idgel™ Precast Gels

Aged precast gels (IDGel™) made on Jun. 4, 2010 are kept at 4° C. until use on Jun. 10, 2011. The electrolyte solution according to the present invention is the same as in Example 1 (EPPS buffer), and it is compared to the classic TGS Laemmli buffer (TGS buffer). The electrophoresis is performed at 180V for 30 minutes (EPPS buffer) or for 40 minutes (TGS buffer). After the electrophoretic run, the migration speed for the migration front to reach the bottom of the gel, and the resolution of a prestained molecular weight marker containing 10 bands weighing between 15 KDa to 175 KDa is measured. The results show that the IDGel™ separated in the EPPS buffer according to the present invention migrated well and displayed sharp and well separated bands. The IDGel™ migrated in the control TGS buffer displayed distinctly fuzzier bands (See no. 20 in FIG. 2). The gel matrix is also distorted during electrophoresis as the gel expands and hangs out of the gel cassette (See no. 30 in FIG. 2). Furthermore, bubbles are apparent between the glass plates of the cassette and the gel due to over-heating (See no. 10 in FIG. 2). The measured temperature in the TGS buffer is 65° C.

Example 3

Gel Electrophoresis of Pagr™ Gold Precast Gels

Figure 3:
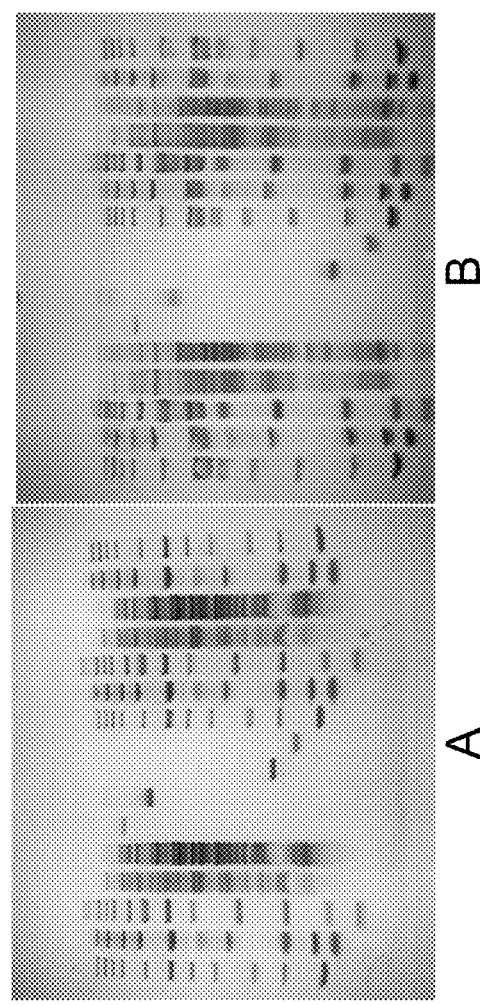
FIG. 3 illustrates polyacrylamide gels electrophoresed in electrolyte solutions according embodiments of the present invention (A) and compared to a gel electrophoresed on Trisglycine-SDS (baseline) solution (B). All the gels electrophoresed were passed their expiry date.

Precast gels (PAGEr™ Gold from Lonza), having an 8-16% acrylamide gradient, 4 months post expiration date, are kept at 4° C. until use. The electrolyte solution according to the present invention is the same as in Example 1 (EPPS buffer), and it is compared to the classic TGS Laemmli buffer (TGS buffer). The electrophoresis is performed at 300V for 21 minutes (EPPS buffer) or at 200V for 74 minutes (TGS buffer). Now referring to FIGS. 3A and B. After the electrophoretic run, the migration speed for the migration front to reach the bottom of the gel, and the resolution of prestained molecular weight markers and other protein samples is compared. The results show that overall, the PAGEr™ Gold gel separated in the EPPS buffer according to the present invention (FIG. 3A) migrated well and displayed sharp and well separated bands. The PAGEr™ Gold gel migrated in the control TGS buffer displayed distinctly fuzzier bands (See FIG. 3B). Since the voltage applied to each gel is different, the PAGEr™ Gold gel separated in the control TGS buffer is expected to complete its migration over a longer lapse of time. However, the PAGEr™ Gold gel separated in the EPPS buffer according to the present invention completed its migration more rapidly than would be expected had identical voltages been applied, with better resolution than the PAGEr™ Gold gel separated in the control TGS buffer.

Example 4

Gel Electrophoresis of an EPPS Precast Gel

Figure 4:
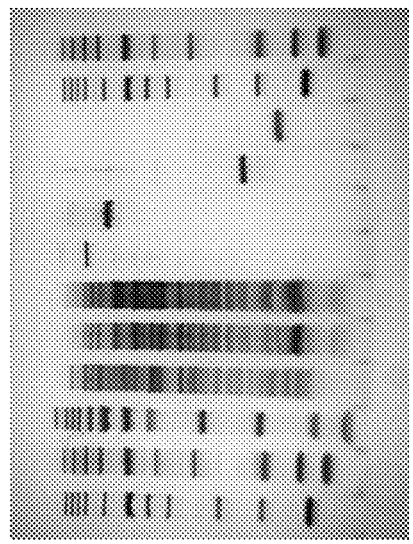
FIG. 4 illustrates a polyacrylamide gel electrophoresed in electrolyte solutions according embodiments of the present invention. The gel electrophoresed is passed its expiry date.

Now referring to FIG. 4. A precast gels (12% acrylamide), containing an EPPS based buffer, having been stored for 13 months at 4° C. until use, is separated in the electrolyte solution according to the present invention is the same as in Example 1 (EPPS buffer). The electrophoresis is performed at 225V for 19 minutes. Now referring to FIG. 4, after the electrophoretic run, the migration speed for the migration front to reach the bottom of the gel, and the resolution of prestained molecular weight markers and other protein samples is evaluated. The results show that overall gel separated in the EPPS buffer according to the present invention migrated well and displayed sharp and well separated bands despite its age.

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:

1. A method of extending a useful electrophoresis life of an electrophoresis gel during an electrophoretic separation of at least one sample comprising the step of:
adding to an electrophoresis buffer containing an electrolyte solution comprising
at least one zwitterion chosen from 2-amino-2methyl-1, 3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino] ethanesulphonic acid) (TES), N-Tris(hydroxymethyl)methyl-3-aminopropanesulfonic acid (TAPS), 3-N-Morpholino propanesulfonic acid (MOPS) and Piperazine-N,N'-bis(2-hydroxypropanesulfonic acid) (POPSO);
Tris(hydroxymethyl)aminomethane (TRIS), wherein the concentration of Tris(hydroxymethyl)aminomethane (TRIS) is 150 mM; and
water,
wherein the pH of the electrolyte solution is from about 8.0 to about 11.0,
at least one different zwitterion chosen from 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino]ethanesulphonic acid) (TES), N-Tris(hydroxymethyl)methyl-3-aminopropanesulfonic acid (TAPS), 3-N-Morpholino propanesulfonic acid (MOPS), and Piperazine-N,N'-bis(2-hydroxypropanesulfonic acid) (POPSO).

2. The method according to claim 1, wherein said zwitterion is 4-(2-hydroxyethyl)piperazine-1-propanesulfonic acid (EPPS or HEPPS).

3. The method according to claim 1, wherein the zwitterion is chosen from N-Glycylglycine (Gly-Gly) and 3-(cyclohexylamino)-2-hydroxy-1-propanesulfonic acid (CAPSO).

4. The method according to claim 1, further comprising the step of applying a voltage to said electrophoresis buffer in contact with an electrophoresis gel containing the at least one sample therein.

5. An electrolyte solution for extending a useful electrophoresis life of an electrophoresis gel comprising:
at least one zwitterion chosen from 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino]ethanesulphonic acid) (TES), 3-N-Morpholino propanesulfonic acid (MOPS), and Piperazine-N,N'-bis(2-hydroxypropanesulfonic acid) (POPSO);
water;

Tris(hydroxymethyl)aminomethane (TRIS), wherein the concentration of Tris(hydroxymethyl)aminomethane (TRIS) is from about 10 mM to about 500 mM;

ethylenediaminetetraacetate (EDTA), wherein the concentration of ethylenediaminetetraacetate (EDTA) is about 0.03% (wt/vol), wherein the pH of the electrolyte solution is from about 8.0 to about 11.0.

6. The electrolyte solution of claim 5, wherein the zwitterion is 4-(2-hydroxyethyl)piperazine-1-propanesulfonic acid (EPPS or HEPPS).

7. The electrolyte solution of claim 5, wherein the zwitterion is chosen from N-Glycylglycine (Gly-Gly) and 3-(cyclohexylamino)-2-hydroxy-1-propanesulfonic acid (CAPSO).

8. The electrolyte solution of claim 5, further comprising sodium dodecyl sulphate (SDS).

9. The electrolyte solution of claim 5, further comprising a second chelating agent selected from the group consisting of ethylene glycol tetraacetic acid (EGTA), trisodium nitrilotriacetate, hydroxyethyl ethylenediamine trisodium acetate (trisodium HEDTA), diethylene triamino pentasodium acetate or uramil disodium acetate.

10. The electrolyte solution of claim 5, wherein the concentration of the zwitterion is from about 1 mM to about 500 mM.

11. The electrolyte solution of claim 10, wherein the concentration of the zwitterion is from about 10 mM to about 500 mM.

12. The electrolyte solution of claim 10, wherein the concentration of the zwitterion is from about 25 mM to about 75 mM.

13. The electrolyte solution of claim 10, wherein the concentration of the zwitterion is from about 50 mM to about 100 mM.

14. The electrolyte solution of claim 13, wherein the concentration of the zwitterion is 50 mM.

15. The electrolyte solution of claim 13, wherein the concentration of the zwitterion is 100 mM.

16. The electrolyte solution of claim 8, wherein the concentration of sodium dodecyl sulphate (SDS) is 0.5% (wt/vol) or less.

17. The electrolyte solution of claim 16, wherein the concentration of sodium dodecyl sulphate (SDS) is 0.1% (wt/vol) or less.

18. The electrolyte solution claim 16, wherein the concentration of sodium dodecyl sulphate (SDS) is 0.1% (wt/vol).

19. A method of extending a useful electrophoresis life of an electrophoresis gel during an electrophoretic separation of at least one sample comprising the step of:

applying a voltage to an electrolyte solution according to claim 5, in contact with an electrophoresis gel containing the at least one sample therein.

20. A method of extending a useful electrophoresis life of an electrophoresis gel during an electrophoretic separation of at least one sample comprising the step of:

adding to an electrophoresis buffer containing an electrolyte solution according to claim 5 at least one different zwitterion chosen from 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl)piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino]ethanesulphonic acid) (TES), N-Tris(hydroxymethyl)methyl-3-aminopropanesulfonic acid (TAPS) and 3-N-Morpholino propanesulfonic acid (MOPS).

21. The method according to claim 20, wherein said zwitterion is 4-(2-hydroxyethyl)piperazine-1-propanesulfonic acid (EPPS or HEPPS).

22. The method according to claim 20, wherein the zwitterion is chosen from N-Glycylglycine (Gly-Gly) and 3-(cyclohexylamino)-2-hydroxy-1-propanesulfonic acid (CAPSO).

23. The method according to claim 20, further comprising the step of applying a voltage to said electrophoresis buffer in contact with an electrophoresis gel containing the at least one sample therein.

* * * * *